United States Patent [19]

Noordam et al.

[11] Patent Number: 5,552,151
[45] Date of Patent: Sep. 3, 1996

[54] STABLE NATAMYCIN SUSPENSIONS

[75] Inventors: Bertus Noordam, Gravenzande; Jacobus Stark, Rotterdam; Ben R. De Haan, Voorburg; Hong Sheng Tan, Bleiswijk, all of Netherlands

[73] Assignee: Gist-brocades B.V., Ma Delft, Netherlands

[21] Appl. No.: 420,021

[22] Filed: Apr. 11, 1995

[30] Foreign Application Priority Data

Apr. 11, 1994 [EP] European Pat. Off. ............ 94200888.9

[51] Int. Cl.⁶ ...................................... A61K 47/36
[52] U.S. Cl. ........................... 424/439; 424/442; 514/937
[58] Field of Search ................... 424/439, 442; 514/937

[56] References Cited

U.S. PATENT DOCUMENTS

| 4,536,494 | 8/1985 | Carter ......................... 514/31 |
| 4,826,822 | 5/1989 | Anderson et al. ............... 536/6.5 |

FOREIGN PATENT DOCUMENTS

| 513922A1 | 11/1992 | Netherlands . |
| 1148801 | 4/1969 | United Kingdom . |
| WO92/00731 | 1/1992 | WIPO . |

OTHER PUBLICATIONS

"Control of slime-forming fungi in industrial water by nystatin-containing compositions", Anderson et al., Braz. Pedido PI, 31 pp. (BR87-1909) (Abstract only).

"Antifungal formulation for foods, agricultural products, and pharmaceuticals", Tan et al., EPA, EP 92-201359 (Abstract only).

*Primary Examiner*—Carlos Azpuru
*Attorney, Agent, or Firm*—Morrison & Foerster LLP

[57] ABSTRACT

Concentrated suspensions of polyene fungicides such as natamycin are disclosed which exhibit good chemical, microbial and physical stability and which are thus particularly suitable as stock suspensions for the preparation of immersion liquids and coating emulsions for treatment of food, feed and agricultural products. Such suspensions have a pH in the range 3 to 4.8 and include a thickening agent.

10 Claims, No Drawings

STABLE NATAMYCIN SUSPENSIONS

This invention relates to chemically, physically and microbially stable concentrated suspensions of polyene fungicides such as natamycin which provide a convenient stock for the easy and reproducible dosage of the fungicide, e.g. to animal feed or grain or for manufacturing liquid preparations to treat food such as cheeses and sausages or to treat agricultural products such as vegetables, fruit and flower bulbs. Further the invention relates to solid compositions of polyene fungicides such as natamycin for preparing such suspensions.

DESCRIPTION OF THE PRIOR ART

For More than 20 years, natamycin has been used to prevent growth of mould on cheeses and sausages.(Ref. 1–3) Cheeses are treated by immersion in a suspension of natamycin in water or covered by an emulsion of a polymer (mostly polyvinyl acetate) in water containing natamycin. Sausages are mainly treated by immersion or by spraycoating with a suspension of natamycinin water. Usually aqueous suspensions for immersion treatments contain 0.1 to 0.2% (w/v) of natamycin, while polymer emulsions for coating purposes contain 0.01 to 0.05% (w/v) of natamycin.

For the production of such suspensions or polymer emulsions, the natamycin may be added directly to the liquids as a powder, for instance by using the wettable powder composition known under the brand name of Delvocid® Instant. Instead of using the powder as such, frequently a concentrated pre-suspension of the natamycin in water is prepared before adding the natamycin to the liquids to be used for treatments. The purpose of preparing a presuspension is to avoid lump formation and to facilitate homogenization of natamycin through the treatment liquids. Mostly these methods of preparing suspensions for treating food are adequate. However, when several types of suspension with varying concentrations of natamycin have to be prepared or several portions of large quantities need to be produced over a longer period such methods are less convenient.

When natamycin is added as a powder to treatment preparations, the laborious weighing of the powder has to be repeated for each type of suspension, thus multiplying the nuisance of possible dust problems.

When a presuspension in water is used to avoid inaccurate dosages, the presuspension has to be agitated continuously to prevent the natamycin from settling down or the presuspension has to be added in total to the treatment preparations. Furthermore, such suspensions are susceptible to undesirable bacterial contamination and cannot be used as a stock for long periods without taking precautions, e.g. addition of a preservative.

A possible way to avoid sedimentation is to make a stock solution of natamycin instead of a suspension. Aqueous solutions of natamycin can be prepared by adjusting the pH of the mixture to a high or a low value. However, under such conditions the stability of natamycin is rather poor (Ref. 4, page 542).

Aqueous suspensions of natamycin are well known in practice. Under the brand name of Pimafucin®, sterile suspensions of natamycin are commercially available as a 1% or a 2.5% presentation in small bottles of up to 100 ml. Pimafucin® is mainly used for medical purposes. To render these suspensions suitable as amultiple dose presentation the suspensions are preserved by using benzalkonium chloride, a preservative of the quaternary ammonium type. Because of the sedimentation of the solid natamycin, such a suspension has to be shaken well every time prior to use. Further to avoid excessive inactivation of the natamycin, the pH of Pimafucin® is usually adjusted to a value of 5.5 to 7.5.

Because of the sedimentation problems and the bacterial vulnerability of known suspensions of natamycin, and the instability of solutions of natamycin, an aqueous stock preparation of natamycin which may be dosed by volumetric methods and which remains stable for a prolonged period, e.g to manufacture treatment liquids for cheeses or sausages, has up till now not been considered a practical proposition.

SUMMARY OF THE PRIOR ART

Suspensions of natamycin are well known. Nevertheless the use of concentrated suspensions to serve as a stock for long periods or even to be used during only one day is not known. This is mainly because of (1) the tendency of the sparingly soluble natamycin to settle down, (2) the chemical instability of natamycin at low and at high pH values and (3) the susceptibility of natamycin suspensions to bacterial growth. Moreover an aqueous solution of natamycin as a stock is not possible because of the instability of natamycin in solution.

OBJECT OF THE INVENTION

The object of this invention is to provide chemically, microbially and physically stable concentrated aqueous stock suspensions of polyene fungicides, in particular natamycin, which are suitable to be used over at least several days without a preservative and without the necessity for complicated equipment either for the preparation or the dosage thereof.

SUMMARY OF THE INVENTION

Unexpectedly it has been found that, without using preservatives, by applying a suitable pH range and using a thickening agent it is possible to produce concentrated aqueous suspensions of polyene fungicides, in particular natamycin, which are chemically and microbially stable for more than 14 days and which have a physical stability of at least several hours.

Surprisingly such suspensions of natamycin have been obtained with a pH of lower than 6, more particularly a pH of lower than 5.1. The pH of a suspension according to the invention will be in the range from 3 to 5.1, preferably from 3.5 to 5.1 and more preferably from 3.5 to 4.5. Thus, a pH of about 4.0 is considered, for example, desirable, although a slightly lower pH, e.g. 3.6 or a slightly higher. pH, e.g. 5.0 is equally acceptable.

The new suspensions are very convenient for use as a stock for the easy and reproducible dosage of natamycin, e.g. for use in the large scale production of coating emulsions for the treatment of cheeses. The concentration of the polyene fungicide in a stock suspension of the invention may be as high as 40% (w/w). Preferably, the concentration of fungicide is from 0.5 to 30%, more preferably from 2 to 25% and most preferably from 5 to 20%.

To provide a suspension with sufficient physical stability, any thickening agent which is known in the art or any combination of such thickening agents may be used. Preferred thickening agents for use in a suspension of the invention are those which have thixotropic or shear thinning and/or pseudoplastic properties such as, for example xanthan, carrageenan, methylcellulose, Arabic gum and combinations thereof.

When a thickening agent without shear thinning properties is used, the viscosity of the suspension is at least about 500 mPa, more preferably from about 1000 to 5000 mPa and most preferably from about 1000 to 3000 mPa. When a thickening agent with shear thinning properties like xanthan is used, the viscosity of the suspension without shear may be more than 50,000 mPa.

Another feature of the invention is a method of forming a suspension of the invention by mixing a solid composition with water. Preferably, wettable powder formulations for this purpose contain at least the polyene fungicide, e.g. natamycin, a thickening agent like xanthan or methylcellulose and preferably a surfactant like sodium dodecyl sulphate. Optionally a buffering system, e.g. of the phosphate and/or of the citrate type, may be incorporated in the powder mixture.

Suspensions of the invention may be used directly to treat a food, feed or agricultural product with a polyene fungicide or may be used to prepare an alternative suspension or coating emulsion for such treatment.

DETAILED DESCRIPTION OF THE INVENTION.

In one aspect, the present invention provides an aqueous suspension of a polyene fungicide having a pH of lower than 6, more particularly a pH of 3 to 5.1, e.g. 3.6 to 5.1 and containing a thickening agent to give a viscosity of at least 500 mPa. Without including a preservative, such an aqueous concentrated suspension of a polyene fungicide, in particular natamycin, will remain chemically and microbially stable for a period of days, e.g. more than 14 days, and exhibit physical stability for at least several hours. By physical stability is meant that stirring is not necessary or that no more than gentle agitation every two hours for 5 minutes will suffice to keep the solid materials from settling down.

As hereinbefore indicated, the concentration of the polyene fungicide in a stock suspension of the invention may be as high as 40% (w/w). Preferably the concentration is from 0.5 to 30%, more preferably from 2 to 25% and most preferably from 5 to 20%. For the preparation of a suspension according to the invention, a polyene fungicide as such may be used or a preparation containing such a fungicide. For instance, the commercially available powder compositions known under the brand name of Delvocid® Instant or Natamax® and containing 50% (w/w) natamycin may conveniently be employed.

Thus, in another aspect, the present invention provides a method of preparing a suspension of the invention which comprises adding appropriate additives including a polyene fungicide and thickening agent, either separately or as a powder composition, to water and mixing, followed if necessary by adjustment of the pH. Preferably, a powder composition comprising the polyene fungicide, the thickening agent, and a surfactant, optionally together with a buffering agent, will be mixed with water, followed if appropriate by pH adjustment.

The invention may be applied to any polyene fungicide.

Thus, suspensions according to the invention may be prepared using not only natamycin but also lucensomycin, nystatin, amphotericin-B and combinations thereof. Preferred fungicides are natamycin, lucensomycin and nystatin.

Any thickening agent which is known in the art or any combination of known thickening agents may in principle be used for the preparation of such suspensions. Examples of suitable thickening agents are xanthan gum, Arabic gum, tragacanth gum, gellan gum, quar gum, locust bean gum, carrageenan gum, rhamxan gum, alginate, polyvinyl acetate and thickening agents of cellulosic origin like hydroxypropylmethylcellulose, hydroxypropylcellulose, carboxymethylcellulose and methylcellulose. Preferred thickening agents are those which have thixotropic or shear thinning and/or pseudoplastic properties such as for example methylcellulose, xanthan gum, carrageenan gum, Arabic gum and combinations thereof.

The thickening agent is preferably used in an amount of from 0.1 to 5.0% (w/w), more preferably from 0.1 to 3.0% (w/w) and most preferably from 0.2 to 2.0% (w/w).

When a thickening agent without shear thinning properties is used, the viscosity of the suspension will be at least about 500 mPa, more preferably from about 1000 to 5000 mPa and most preferably from about 1000 to 3000 mPa. When a thickening agent with shear thinning properties like xanthan is used, the viscosity of the suspension without shear may be more than 50,000 mPa, while the viscosity under shear will be dependent on the applied shear.

Advantageously, a suspending agent is used which serves as a deflocculant. Suitable suspending agents are for instance microcrystalline cellulose-sodium carboxymethylcellulose (Avicel® RC), sodium dodecyl sulphate, polyethylene glycol, fumed silica, glycol and glycerol.

The pH of a suspension according to the invention may be adjusted by any method known in the art, e.g. by adding an acidic or an alkalic compound or by using a buffering system. Useful acids are for example citric acid, lactic acid, ascorbic acid, hydrochloric acid, phosphoric acid, sulphuric acid and tartaric acid. Useful basic compounds are for example sodium hydroxide, potassium hydroxide, ammonia and calcium hydroxide. Useful buffering systems are for instance those of the phosphate and/or of the citrate type.

As indicated above, a solid powder composition for combination With water to provide a suspension according to the invention should preferably at least contain the polyene fungicide, a thickening agent like xanthan or methylcellulose, and optionally a surfactant like sodium dodecyl sulphate. The presence of a buffering system in the solid powder composition may be of advantage, but is not essential. The formulation may also contain components which are already present in a starting polyene fungicide preparation. For example, when Delvocid® Instant or Natamax® is used as a source of natamycin, lactose will also be present in the final blend.

The amount of the polyene fungicid® such as natamycin trihydrate in a solid compositions for use in the preparation of a suspension of the invention may be up to 99.8% (w/w), e.g. 80 to 99.8% (w/w), preferably up to 99.5%. Preferably the amount of the thickening agent in such a solid composition is from 0.2 to 20% (w/w), more preferably from 0.5 to 10% (w/w). The amount of the surfactant is preferably from 0.1 to 2% (w/w), more preferably from 0.2 to 1% (w/w). A buffering system may be present at up to 20% (w/w). Useful buffering systems may consist of one or more of citric acid, the mono-, di-, and trisodium salts of citric acid and the mono- and disodium salts of phosphoric acid. Finally, it is obvious that filling agents like. lactose and/or cellulose may also be present in the final solid composition.

After mixing the solid powder composition with water to give a stock suspension, if necessary, the pH of the resulting mixture will be adjusted to an appropriate value by methods known per se.

In further aspects, the present invention provides use of a suspension according to the invention directly for treatment of a food, feed or agricultural product or for the preparation of a treatment liquid or coating emulsion for such treatment.

As stated above, suspensions prepared in accordance with the present invention are very convenient for use as a stock suspension. For example, such suspensions are very useful for preparing immersioh liquids for treating food and for the large scale production of coating emulsions for the treatment of cheeses. Further, such suspensions are convenient for use as part of a continuous process, e.g. to produce coating emulsions for the treatment of feed. Moreover neither for their preparation or their application is complicated equipment required. Mostly, the use of a simple stirring device will satisfy. An additional advantage of using a suspension according to the invention as a stock for preparation of treatment liquids is that dust problems and lump forming are minimized.

Embodiments of the present application are illustrated by the following examples.

EXAMPLE 1

This example demonstrates the microbial and chemical stability of suspensions according to the invention.

1a. 100 g of Delvocid® Instant (containing 50% of natamycin), 0.1 g of sodium dodecyl sulphate and 10 g of methylcellulose 400 CP (Sigma) were mixed together. The mixture was then suspended into 390 ml of water using a magnetic stirrer. The pH of the suspension was adjusted to 4.8 by means of a 1N solution of hydrochloric acid.

1b. The experiment was repeated except that the pH was adjusted to 4.4 instead of 4.8.

1c. The experiment was repeated except that the pH was adjusted to 4.0 instead of 4.8.

1d. The experiment was repeated except that the pH was adjusted to 3.6 instead of 4.8.

1e. The above experiment was repeated except that the pH was adjusted to 4.0 using a solution of acetic acid instead of hydrochloric acid.

1f. 100g of Delvocid® Instant, 0.1 g of sodium dodecyl sulphate, 10g of methylcellulose 400 cp and 0.1 g of ascorbic acid were mixed together and then suspended into 390 ml of water. The pH of the suspension was adjusted to 4 by means of a 1N solution of sodium hydroxide.

50 ml of each of the above mixtures were inoculated with a mixture of respectively $3.4 \times 10^6$ CFU/ml of *Staphylococcus aureus* ATCC 6538, $2.9 \times 10^6$ CFU/ml of *Escherichia coli* ATCC 11229, $5.5 \times 10^4$ CFU/ml of *Bacillus cereus* ATCC 2 and $1.5 \times 10^5$ CFU/ml of *Lactococcus lactis* ATCC 19257. After incubation at 25° C. for 14 days, the total cell count was estimated using methods known per se. Composition 1a had a total cell count of more than $10^7$ CFU/ml while the other compositions contained less than 200 CFU/ml.

The above results showed that a pH value of lower than 4.8 is sufficient to inhibit bacterial growth.

The natamycin content of each suspension was estimated by HPLC immediately after preparation and after 13 days storage at 25° C. None of the six mixtures showed a decline in the natamycin concentration.

EXAMPLE 2

In this experiment the effect of viscosity on the sedimentation of natamycin was investigated.

Aqueous suspensions containing 20% (w/w) of Delvocid® Instant, 0.1% (w/w) of sodium dodecyl sulphate and respectively 1.8%, 1.6% and 1.4% (w/w) of methylcellulose 400 cp and with 0.7% of methylcellulose 4000 cp were prepared according to the method described in Example 1. The pH of the suspensions was adjusted to 4.0 by means of a 1N solution of hydrochloric acid.

The viscosities of the resulting suspensions as measured with a Brookfield viscosimeter were respectively 2740, 1910, 1080 and 2380 mPa.

To check the sedimentation of the natamycin, 100 ml of each of the suspensions was put into a measuring cylinder of 100 ml. The phase separation was judged visually. No phase separation was observed during more than 8 hours for the suspension with the lowest viscosity (1080 mPa) and during more than 24 hours for the other four mixtures.

EXAMPLE 3

106 g of natamycin trihydrate, 4 g of xanthan gum (Keltrol® RD, Kelco International Limited) and 0.5 g of sodium dodecyl sulphate were mixed together and then added to 990 ml of water. After stirring the mixture for 30 minutes, the pH was adjusted to 4.0 by means of a 1N solution of hydrochloric acid.

The sedimentation characteristics were checked visually by putting 100 ml of the resulting suspension into a measuring cylinder of 100 ml. Even after two weeks standing no phase separation was observed.

The microbial and chemical stability was checked in the same way as described in Example 1.

After incubation at 25° C. for 14 days, the microbial cell count was less than 200 CFU/ml. HPLC analysis showed that the natamycin content immediately after preparation and after storage at ambient temperature for 14 days was respectively 10.2 and 10.0% (w/w).

EXAMPLE 4

200 g of Delvocid® Instant, 0.2 g of sodium dodecyl sulphate and 4 g of Keltrol® RD were mixed together and then suspended into 796 ml of water by stirring for 30 minutes. The pH of the suspensions was adjusted to 4.0 by means of a 1N solution of hydrochloric acid.

The resulting suspension showed no sedimentation after standing for more than 14 days. The microbial and chemical stability was checked in the same way as described in Example 1. After incubation at 25° C. for 14 days, the microbial cell count was less than 200 CFU/ml. HPLC analysis showed that the natamycin content immediately after preparation and after storage at ambient temperature for 14 days was respectively 10.5 and 10.7% (w/w).

EXAMPLE 5

A wettable powder of the following composition was produced in a Turbula® mixer: 100 g of natamycin trihydrate, 100 g of lactose, 4 g of Keltrol® RD, 1 g of sodium dodecyl sulphate, 1 g. of citric acid and 0.1 g of trisodium-citrate dihydrate. The components were mixed together.

The wettable powder is suspended into 800 ml of water giving a total volume of 1000 ml and stirred for 30 minutes.

The pH of the suspension was measured immediately after preparation and after 14 days storage in the dark at room temperature. In both cases the pH was 4.04.

Sedimentation characteristics were checked in the same way as described in Example 3. The suspension showed no sedimentation after standing for more than 14 days.

The microbiological stability was checked using the well known challenge test method.

Five samples of 50 ml of the suspension were inoculated with respectively $3.8 \times 10^3$ CFU/ml of *Escherichia coli* ATCC 11229, $7.7 \times 10^3$ CFU/ml of *Staphylococcus aureus* ATCC 6538, $1.5 \times 10^4$ CFU/ml of *Listeria monocytogenes* DSM 20500, $9.2 \times 10^3$ CFU/ml of *Bacillus cereus* ATCC 2 and $1.8 \times 10^3$ CFU/ml of *Lactococcus lactis* ATCC 19257.

After incubation at 30° C. for 1 hour, 7 days and 14 days samples were taken and the total cell count of each sample was determined using well known methods.

All samples contained less than 10 CFU/ml, which demonstrates that the suspension is microbiological stable for at least 14 days.

The natamycin content of the suspension was estimated by HPLC immediately after preparation and after 14 days storage in the dark at ambient temperature. The natamycin content in both cases was 10.4% (w/w).

EXAMPLE 6

A wettable powder with the same composition as described in Example 5 was prepared and stored for more than months at room temperature.

A natamycin suspension was produced as described in Example 5.

The results concerning physical, microbiological and chemical stability were the same as described in Example 5.

EXAMPLE 7

A wettable powder of the following composition was produced in a Turbula® mixer: 106 g of natamycin trihydrate, 8.3 g of lactose, 1 g of Keltrol® RD, 0.5 g of citric acid and 0.055 g of sodiumcitrate dihydrate. The components were mixed together. 54 g of the wettable powder was suspended into 196 ml of water by stirring for 30 minutes (suspension A).

From the half of suspension A the pH was adjusted to 6.5 by means of a 4N solution of NaOH (suspension B).

The pH of suspension A was measured immediately after preparation (pH=4.87) and after 14 days storage in the dark at room temperature (pH=5.04).

Sedimentation characteristics of suspension A were checked in the same way as described in example 3. The suspension showed no sedimentation after standing for more than 14 days.

After incubation at room temperature the total cell count of suspension A was determined after 1 hour, 7 days and 14 days using well known methods.

All samples contained less than 10 CFU/ml, which demonstrates that the suspension is microbiological stable for at least 14 days.

After incubation at room temperature the total cell count of suspension B was more than $10^7$ CFU/ml after 4 days.

The above results showed that a pH value of higher than 6.5 is insufficient to inhibit bacterial growth.

The natamycin content of suspension A was estimated by HPLC immediately after preparation and after 14 days storage in the dark at ambient temperature. The natamycin content was respectively 18.0 and 18.1% (w/w).

References

1. Daamen, C.B.G. and Berg, G. van den; "1. Prevention of mould growth on cheese by means of natamycin" Voedingsmiddelentechnologie, 18 (2), 26 (1985)

2. Morris, H. A. and Castberg, H. B.; "Control of surface growth on Blue cheese using pimaricin" Cultured Diary Products Journal, 15 (2), 21 (1980)

3. Morris, H. A. and Hart, P. A.; "Pimaricin—What is it?" Cultured Dairy Products Journal 13 (3), 22 (1978)

4. Brik, H.; "Natamycin" Analytical Profiles of Drug Substances 10, 513–561, (1984)

We claim:

1. An aqueous fungicide composition comprising a suspension of 0.5 to 40% (w/w) of a polyene fungicide and from 0.2 to 5% (w/w) of a thickening agent wherein said composition has a pH of 3 to less than 6 and said composition has a viscosity of at least about 500 mPa.

2. The fungicide composition of claim 1, wherein said composition has a pH 0f3.6 to 5.1.

3. The fungicide composition of claim 1 wherein said thickening agent is present to give a viscosity of at least about 1000 mPa.

4. The fungicide composition of claim 1 wherein the thickening agent comprises one or more agents selected from the group consisting of xanthan gum, Arabic gum, tragacanth gum, gellan gum, quar gum, locust bean gum, carrageenan gum, rhamxan gum, alginate, polyvinylacetate, hydroxypropylmethylcellulose, hydroxypropylcellulose carboxymethylcellulose, and methylcellulose.

5. The fungicide composition of claim 1 which additionally contains a surfactant.

6. The fungicide composition of claim 1 wherein the polyene fungicide is natamycin.

7. A method to prepare the fungicide composition of claim 1 which comprises the steps of adding a polyene fungicide and a thickening agent, separately or together as a powder composition to water and mixing and adjusting the pH to obtain a pH from 3 to less than 6 if the pH is less than 3 or 6 or greater.

8. A method to prepare a treatment liquid or coating emulsion for treatment of a food, feed or agricultural product which method comprises the step of stirring the fungicide composition of claim 1 into an aqueous diluent.

9. A method for protecting a food, feed or agricultural product against mold growth which method comprises the step of applying to said food, feed or agricultural product an effective amount of the fungicide composition of claim 1 or an aqueous diluted form thereof.

10. A food, feed or agricultural product having applied thereto an amount of the fungicide composition of claim 1 or a diluted form thereof effective to prevent mold growth.

* * * * *